(12) United States Patent
Locke et al.

(10) Patent No.: US 9,320,673 B2
(45) Date of Patent: *Apr. 26, 2016

(54) COMPONENT MODULE FOR A REDUCED PRESSURE TREATMENT SYSTEM

(71) Applicant: KCI Licensing, Inc., San Antonio, TX (US)

(72) Inventors: Christopher Brian Locke, Bournemouth (GB); Timothy Mark Robinson, Basingstoke (GB); Mark Stephen James Beard, Ferndown (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/668,736

(22) Filed: Mar. 25, 2015

(65) Prior Publication Data

US 2015/0245974 A1 Sep. 3, 2015

Related U.S. Application Data

(63) Continuation of application No. 14/307,665, filed on Jun. 18, 2014, now Pat. No. 9,019,681, which is a continuation of application No. 13/350,615, filed on Jan. 13, 2012, now Pat. No. 8,786,999, which is a (Continued)

(51) Int. Cl.
*H01H 47/00* (2006.01)
*A61H 9/00* (2006.01)
(Continued)

(52) U.S. Cl.
CPC ........... *A61H 9/0057* (2013.01); *A61M 1/0001* (2013.01); *A61M 1/0023* (2013.01);
(Continued)

(58) Field of Classification Search
CPC ....................................................... F23N 5/123
USPC ......................................................... 361/170
See application file for complete search history.

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery.

(Continued)

*Primary Examiner* — Stephen W Jackson

(57) ABSTRACT

A reduced pressure treatment system includes a control unit having a control system and a reduced pressure source. The reduced pressure treatment system further includes a manifold unit in fluid communication with the reduced pressure source and a component module to augment treatment. The component module is configured to communicate with the control system of the control unit, and the component module includes a first mounting region configured to be coupled to a complimentary mounting region of the control unit. The component module further includes a second mounting region identical to the complimentary mounting region of the control unit to allow a second component module to be coupled to the first component module.

41 Claims, 9 Drawing Sheets

Related U.S. Application Data continuation of application No. 12/986,974, filed on Jan. 7, 2011, now Pat. No. 8,098,473, which is a continuation of application No. 11/901,602, filed on Sep. 18, 2007, now Pat. No. 7,876,546.

(60) Provisional application No. 60/845,993, filed on Sep. 19, 2006.

(51) Int. Cl.

| | |
|---|---|
| *A61M 5/14* | (2006.01) |
| *F16M 11/04* | (2006.01) |
| *F16M 13/02* | (2006.01) |
| *A61M 1/00* | (2006.01) |
| *G01F 23/14* | (2006.01) |
| *A61N 1/04* | (2006.01) |
| *A61N 5/06* | (2006.01) |

(52) U.S. Cl.
CPC ............ *A61M1/0025* (2014.02); *A61M 1/0031* (2013.01); *A61M 1/0088* (2013.01); *A61M 5/1415* (2013.01); *A61N 1/0468* (2013.01); *A61N 5/0616* (2013.01); *F16M 11/046* (2013.01); *F16M 11/048* (2013.01); *F16M 13/02* (2013.01); *G01F 23/14* (2013.01); *A61H 2201/5056* (2013.01); *A61M 2205/15* (2013.01); *A61M 2205/33* (2013.01); *A61M 2205/3327* (2013.01); *A61M 2205/3331* (2013.01); *A61M 2205/3337* (2013.01); *A61M 2205/3379* (2013.01); *A61M 2205/43* (2013.01); *A61M 2205/581* (2013.01); *A61N 2005/0661* (2013.01); *F16M 2200/027* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,696,662 B2 * | 4/2014 | Eder ............... A61B 18/1442 606/45 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755495 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |

(56) References Cited

FOREIGN PATENT DOCUMENTS

| | | |
|---|---|---|
| EP | 0358302 A2 | 3/1990 |
| EP | 1018967 A1 | 7/2000 |
| GB | 692578 A | 6/1953 |
| GB | 2 195 265 A | 4/1988 |
| GB | 2 197 789 A | 6/1988 |
| GB | 2 220 357 A | 1/1990 |
| GB | 2 236 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1): Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp, 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-135, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatmean of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Docker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prey. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Soiovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

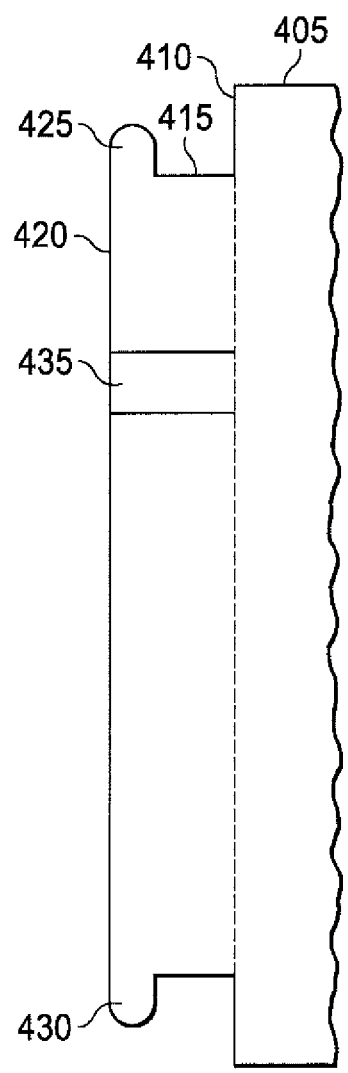
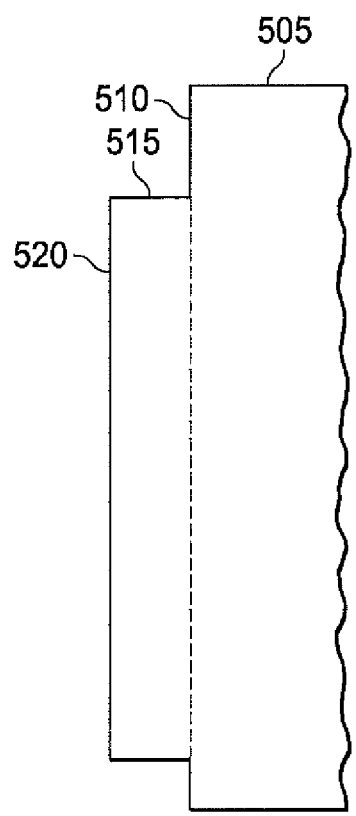
FIG. 4
FIG. 5

COMPONENT MODULE FOR A REDUCED PRESSURE TREATMENT SYSTEM

CROSS-REFERENCE TO RELATED APPLICATIONS

This application is a continuation of U.S. patent application Ser. No. 14/307,665, filed Jun. 18, 2014, which is a continuation of U.S. patent application Ser. No. 13/350,615, filed Jan. 13, 2012, now U.S. Pat. No. 8,786,999, which is a continuation of U.S. patent application Ser. No. 12/986,974, filed Jan. 7, 2011, now U.S. Pat. No. 8,098,473, which is a continuation of U.S. patent application Ser. No. 11/901,602, filed Sep. 18, 2007, now U.S. Pat. No. 7,876,546, which claims the benefit of U.S. Provisional Application No. 60/845,993, filed Sep. 19, 2006, all of which are hereby incorporated by reference.

BACKGROUND OF THE INVENTION

1. Field of the Invention

The present invention relates generally to tissue treatment systems and in particular to a component module for a reduced pressure treatment system.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold unit. The porous pad contains cells or pores that are capable of distributing reduced pressure to the tissue and channeling fluids that are drawn from the tissue. The porous pad often is incorporated into a dressing having other components that facilitate treatment.

While existing reduced pressure treatment systems have enjoyed wide commercial and medical success, it would be advantageous to expand the functionality of these systems to provide a more comprehensive treatment regimen.

A need exists, therefore, for an expandable reduced pressure treatment system that allows component modules to be combined with the expandable reduced pressure treatment system and other modules to provide additional treatment features and options.

BRIEF SUMMARY OF THE INVENTION

The limitations of conventional reduced pressure treatment systems are improved by the systems and methods described herein. In one embodiment, a reduced pressure treatment system for treating a tissue site of a patient includes a control unit having a control system and a reduced pressure source. The reduced pressure treatment system further includes a manifold unit in fluid communication with the reduced pressure source and a component module to augment treatment. The component module is configured to communicate with the control system of the control unit, and the component module includes a first mounting region configured to be coupled to a complimentary mounting region of the control unit. The component module further includes a second mounting region identical to the complimentary mounting region of the control unit to allow a second component module to be coupled to the first component module.

In another embodiment, a reduced pressure treatment system for treating a tissue site of a patient includes a control unit having a control system and a reduced pressure source. A manifold unit is in fluid communication with the reduced pressure source, and a plurality of component modules are provided to augment treatment. Each of the plurality of component modules is configured to communicate with the control system, and at least one of the plurality of components modules is configured to be coupled to both the control unit and another of the plurality of component modules.

Other objects, features, and advantages of the embodiment described herein will become apparent with reference to the drawings and detailed description that follow.

BRIEF DESCRIPTION OF THE DRAWINGS

FIG. 4 illustrates an enlarged partial cross-section view of a control unit similar to the control unit of FIG. 3 along line 4-4;

FIG. 5 illustrates an enlarged partial cross-section view of a control unit similar to the control unit of FIG. 3 along line 5-5;

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, and electrical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

In the context of this specification, the term "reduced pressure" generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

Figure 1:
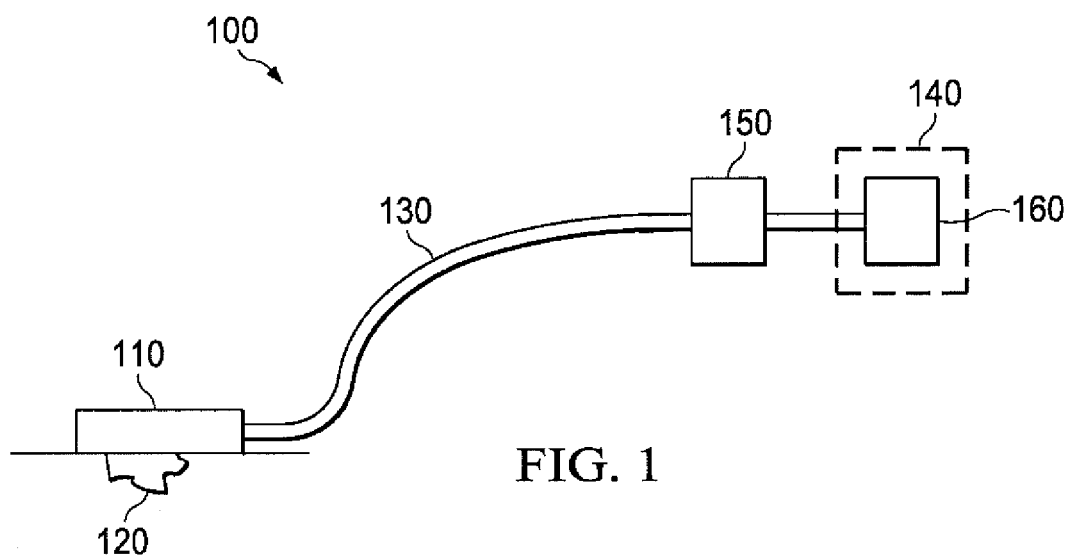
FIG. 1 is a schematic diagram of a reduced pressure treatment system according to an embodiment of the present invention.

FIG. 1 is a schematic diagram of a reduced pressure treatment system 100 according to the present invention. The reduced pressure treatment system 100 comprises a dressing 110, which generally includes a manifold unit that is applied to, or within, a tissue site 120 for treatment. The dressing 110 is fluidly connected to a reduced pressure source 160 by a conduit 130. In certain embodiments, the reduced pressure source 160 may be integrated with a reduced pressure control unit 140, as described below, and the reduced pressure treatment system 100 may also include a canister 150 for collecting liquid and other non-gaseous exudates extracted from the tissue site.

Figure 2:
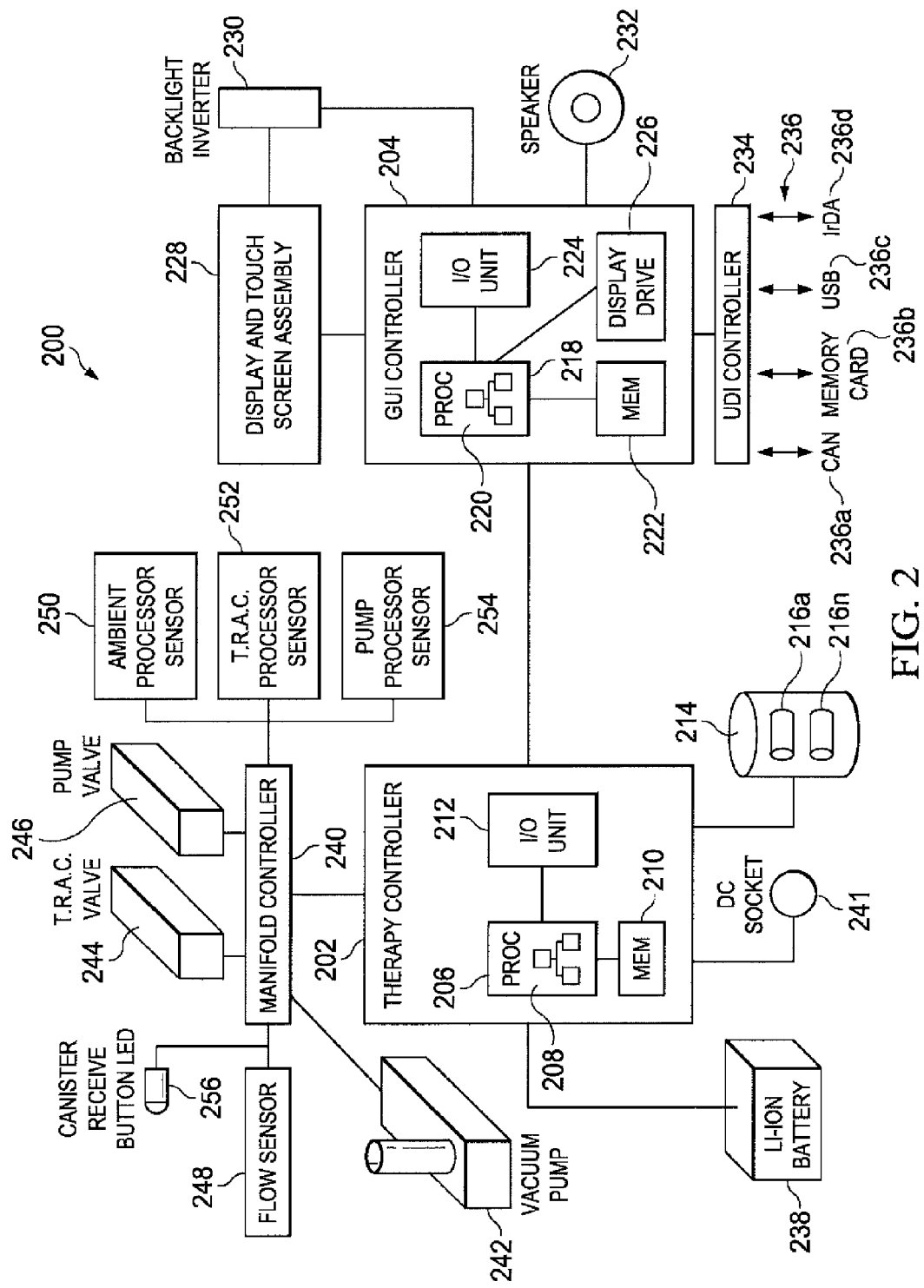
FIG. 2 is a block diagram of an exemplary control system of a reduced pressure control unit according to an embodiment of the present invention.

FIG. 2 is a block diagram of an exemplary control system 200 of the reduced pressure control unit 140. The control system 200 includes a treatment controller 202 and a graphical user interface (GUI) controller 204. The treatment controller 202 may include one or more processors 206 that execute software 208. The processor(s) 206 may be in communication with a memory 210 and input/output (I/O) unit 212. The software 208 may be configured to control a number of different operations of the reduced pressure treatment system 100, such as controlling tissue treatment, monitoring sensors and generating alarms and performing communications with systems and devices external to the control unit 140 in conjunction with the I/O unit 212 and GUI controller 204. It should be understood that the software 208 may further be configured to perform different and/or other functions.

The I/O unit 212 may enable the control system 200 to communicate with external modules, systems, and networks, for example. In one embodiment, the I/O unit 212 may operate in conjunction with a controller area network (CAN) or modified CAN, as described further herein. The processor 206 may further execute software to receive and process CAN data being received via the I/O unit 212.

A storage unit 214, such as a disk drive or storage medium, may be in communication with the treatment controller 202. Databases 216a-216n (collectively 216) may be used to store treatment or other information. The databases may be configured as relational databases or otherwise. Other information, such as software, may be stored on the storage unit 214.

The GUI controller 204 may include one or more processors 218 that execute software 220. The software 220 may be configured to generate a graphical user interface with which an operator, patient, technician, or other user may interface to control the system 100. The processor 218 may be in communication with a memory 222, I/O unit 224, and display driver 226. The memory 222 may store current parameters associated with displaying the GUI. For example, if the GUI is being used to display a particular screen shot, the screen shot may be stored in the memory 222. The I/O unit 224 may be used to interface with the treatment controller 202 and other devices.

A display and touch screen assembly 228 may be connected to the GUT controller 204 and be used to display the GUI generated by the GUI controller 204. The screen 228 enables an operator to merely touch the screen with his or her finger or stylus, as understood in the art, to interface with the GUI. By providing a touch screen, inclusion of a keyboard or keypad may be avoided. However, it should be understood that an external keyboard or keypad may be utilized in accordance with the principles of the present invention. A backlight inverter 230 may be connected to the GUI controller 204 and screen assembly 228. Alternatively, the backlight inverter 230 may be incorporated into the screen assembly 228. In operation, the backlight inverter may enable the screen assembly 228 to be inverted for different ambient lighting conditions. For example, a user of the system 100 may be treating a patient at night and use backlight inverter 230 to selectively turn on the backlight of the screen assembly 228 so that he or she can see the GUI better. Alternatively, the backlight inverter may be used to turn the light on the screen assembly 228 off at night to allow a patient to sleep in a darker environment.

A speaker 232 may be in communication with the GUI controller 204. The speaker may be used to provide sound notification to the user when action is required, or when an alarm condition has occurred.

A unified display interface (UDI) 234 may be utilized in accordance with the principles of the present invention. The UDI 234 may be used as a digital video interface to assist with video presentation. In addition, a number of communication ports 236 may be provided to enable a user to connect external devices to the control system 200. For example, the input ports 236 may include a CAN port 236a to enable the control system 200 to interface with other treatment systems, memory card port 236b to enable a user to transport data from one device to another, universal serial bus (USB) port to enable an operator to connect devices to the control system 200, such as printers, and Infrared Data Association (IrDA) port 236d to enable a user to interface other devices configured with an IrDA port to the system. It should be understood that other communication ports currently available or available in the future may be utilized in accordance with the principles of the present invention. For example, a communication port for connecting to a local or wide area network may be provided to enable a user to connect the control system 200 to a network.

A controller area network is a communication bus that was originally developed for automotive applications in the early 1980s. The CAN protocol was internationally standardized in 1993 as ISO 11898-1 and includes a data link of the seven layer IOS/OSI reference model. CAN, which is now available from a large number of semiconductor manufacturers in hardware form, provides two communication services: (i) sending a message (data frame transmission) and (ii) requesting a message (remote transmission request, RTR). All other services, such as error signaling and automatic re-transmission of erroneous frames, are user-transparent, which means that the CAN circuitry automatically performs these services without the need for specific programming.

A CAN controller is comparable to a printer or typewriter. Language, grammar, and vocabulary is defined for a particular use. CAN provides a multi-master hierarchy that allows for building of intelligent and redundant systems. The use of CAN with the tissue treatment system enables additional component modules, as described further herein, to operate in conjunction with the system. The component modules may operate as nodes, where each node on the CAN receives messages and decides whether a message is relevant. Data integrity is maintained because all devices in the system receive the same information. CAN also provides sophisticated error detection mechanisms and re-transmission of faulty messages.

In one embodiment, the language, grammar, and vocabulary may be customized for the system so that only devices that have the same language, grammar, and vocabulary can communicate with the system. By operating with such a customized or proprietary system, control over the quality of modules and devices that interface with the system may be maintained.

Referring still to FIG. 2, in operation, the communication ports 236 may be utilized to enable users to import or export data to and from the control system 200. For example, patient information, treatment information, and images associated with patient wounds may be communicated over a communication port 236. Other information, including software updates, may be communicated over one or more communication ports 236.

A lithium-ion (Li-Ion) battery 238 and DC socket 241 may be connected to the therapy controller 202. An external adapter (not shown) may be connected to a wall socket (not shown) to convert AC power to DC power for supplying DC power to the treatment controller 202 and other electrical components within the control system 200. If the external power should fail, then the Li-Ion battery 238 powers the control system 200. Alternatively, should the control system 200 be used in a location without power or be used in reliance on battery power, the Li-Ion battery 238 provides power to the control system 200.

A manifold controller 240 may be connected to the treatment controller 202 and be used to control various devices of the dressing 110 and receive feedback information from sensors disposed on the dressing 110. The manifold controller 240 may communicate with the treatment controller 202 while performing treatment. The manifold controller 240 may include analog and digital circuitry (not shown) for communicating with the various devices on the dressing 110. In one embodiment, the manifold controller 240 may include one or more digital-to-analog (D/A) and analog-to-digital (A/D) converters (not shown) to enable digital and analog signals to be passed between the various devices (e.g., sensors) on the dressing 110. Still yet, one or more amplifiers (not shown) may be included with the manifold controller 240.

As shown, a number of transducers (i.e., sensors) and devices may be connected to the manifold controller 240. A reduced pressure source, such as a vacuum pump 242, may be connected to the manifold controller 240. A valve 244 and pump valve 246 may be connected to the manifold controller 240 and used to control air being moved within the manifold unit. A number of sensors may also be connected to the manifold controller 240, including a flow sensor 248, ambient pressure sensor 250, feedback pressure sensor 252, and pump pressure sensor 254. These sensors may be conventional airflow and pressure sensors as understood in the art. A canister release button LED 256 may also be connected to the manifold controller 240.

In operation, the manifold controller 240 may communicate signals between the treatment controller 202 and devices coupled to the dressing 110. In communicating the signals, the manifold controller 240 may condition the signals by converting the signals between analog and digital signals, amplify signals and amplify drive signals for the vacuum pump 242 and valves 244 and 246. In one embodiment, the manifold controller 240 includes a processor (not shown) to perform local processing and control to offload some of the processing and control the processor 206 of the treatment controller 202.

Figure 3:
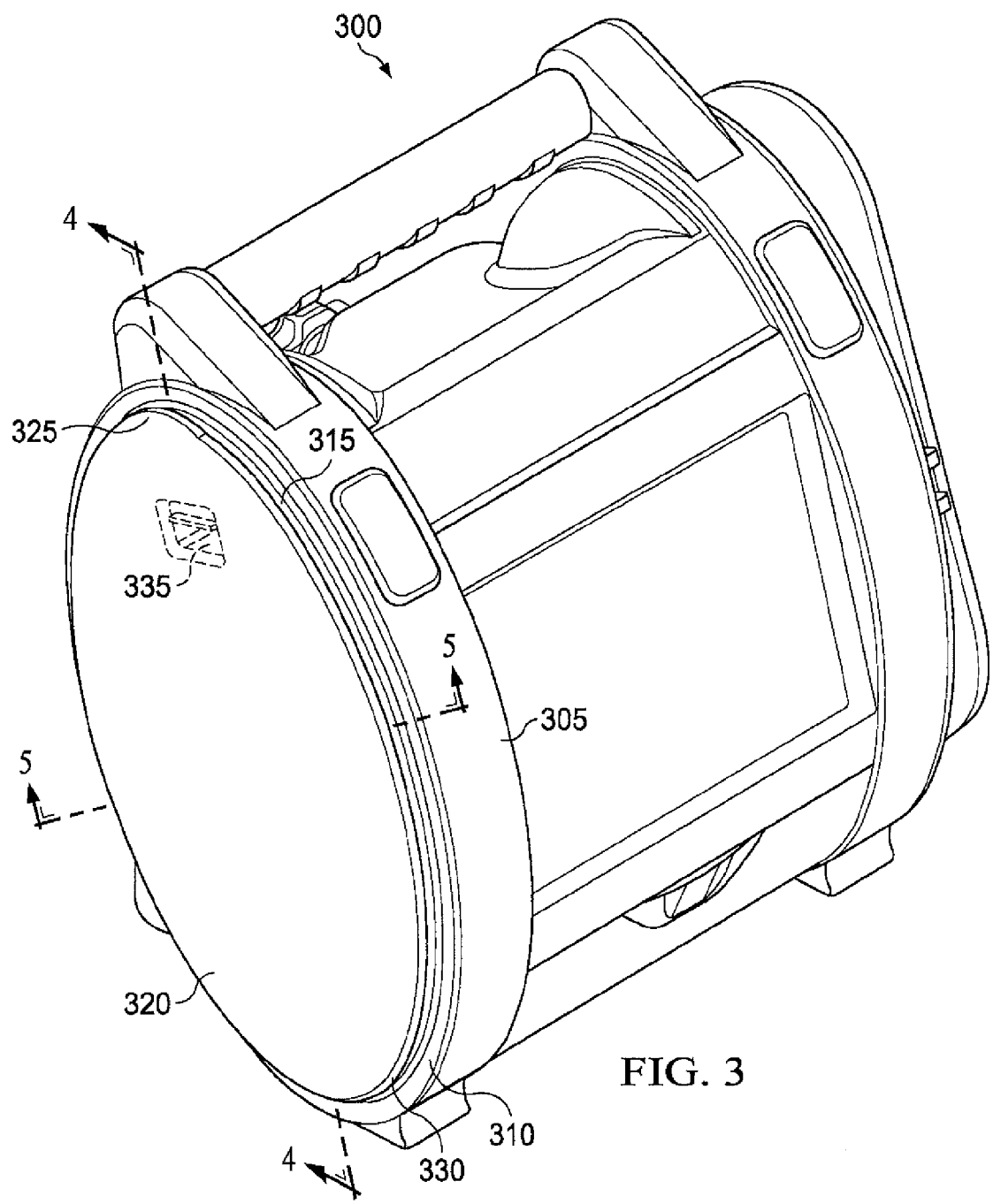
FIG. 3 illustrates a front perspective view of one embodiment of a control unit that houses the control system of FIG. 2.

FIG. 3 is a front perspective view of one embodiment of a control unit 300 that houses the control system 200. As FIG. 3 illustrates, the control unit 300 includes a housing 305 having a shoulder 310 and an extension 315. The extension 315 includes an end surface 320, a first ridge 325, and a second ridge 330. The second ridge is generally located on the end surface 320 substantially opposite the first ridge 325. The general steps of the control unit 300 illustrated in FIG. 3 is an elliptic cylinder, but any geometric configuration that provides sufficient interior capacity for the control system 200 and the reduced pressure source 160 is acceptable. The extension 315 includes an aperture 335, through which the CAN port 236a is exposed to the exterior of the end surface 320.

FIG. 4 is an enlarged partial cross-section view of a control unit similar to the control unit 300 along line 4-4. In particular, FIG. 4 illustrates a partial housing 405 having a shoulder 410 and an extension 415. The extension 415 includes an end surface 420, a first ridge 425, and a second ridge 430 substantially opposite the first ridge 425. An aperture 435 extends from the exterior of the end surface 420 to the interior of the housing 405.

FIG. 5 is an enlarged partial cross-section view of a control unit similar to the control unit 300 along line 5-5. In particular, FIG. 5 illustrates a partial housing 505 having a shoulder 510 and an extension 515 with an end surface 520.

In any embodiment of the control unit, the housing may be manufactured as separate components and subsequently assembled, or may be manufactured as a single unit.

Figure 6:
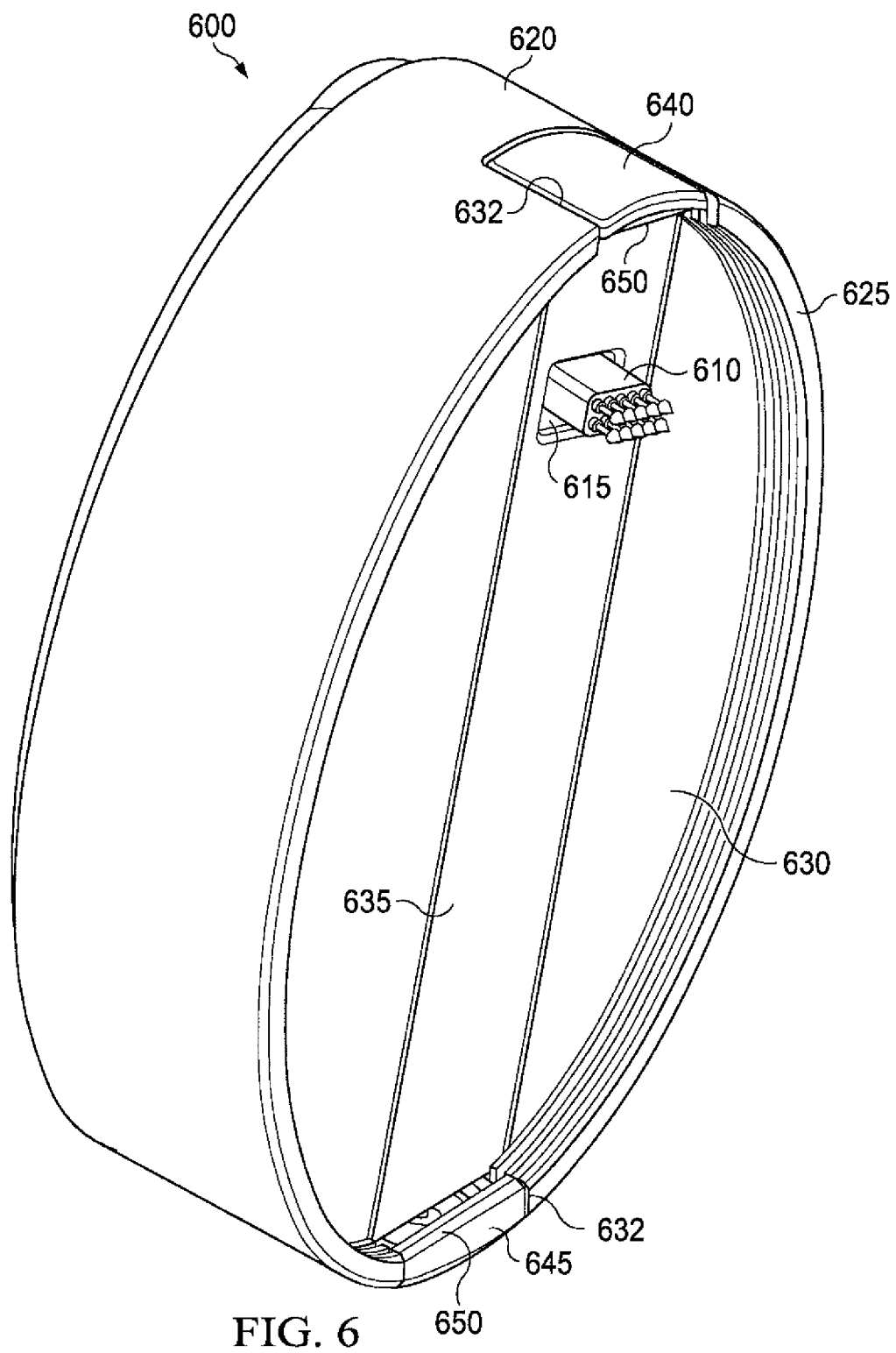
FIG. 6 illustrates a perspective view of a first end of a component module according to an embodiment of the present invention.

FIG. 6 is a perspective view of a first end of an embodiment of a component module 600. The component module 600 may include a variety of equipment that is useful for tissue treatment, including without limitation a wound camera, cyclic/next generation skin stretching, capacitive volume and wound contour mapping, wound bed pH monitoring, wound warming/climate control, wound moisture and temperature monitoring, electrical stimulation, UV therapy, and wound healing marker measurement. The component module 600 typically includes a control system similar to the control system 200 described above. In particular, the component module 600 includes a CAN controller (not shown) and a CAN port (see FIG. 7). The component module 600 also includes a CAN plug 610, which protrudes through an aperture 615 and interfaces with the CAN port 236a of the control system 200. As FIG. 6 illustrates, the component module 600 includes a housing 620 having a rim 625, a recessed end surface 630, and notches 632. The component module 600 further includes a mounting assembly 635 fixed to the recessed end surface 630. The mounting assembly 635 includes a first latch 640 and a second latch 645 that are positioned within the notches 632. The first latch and the second latch each have a fastener bar 650 that is substantially flush with the rim 625 in the configuration illustrated in FIG. 6. The fastener bars 650 are configured to overlap the ridges on other modules or on a control unit, such as ridges 425 and 430 illustrated in FIG. 4.

Figure 7:
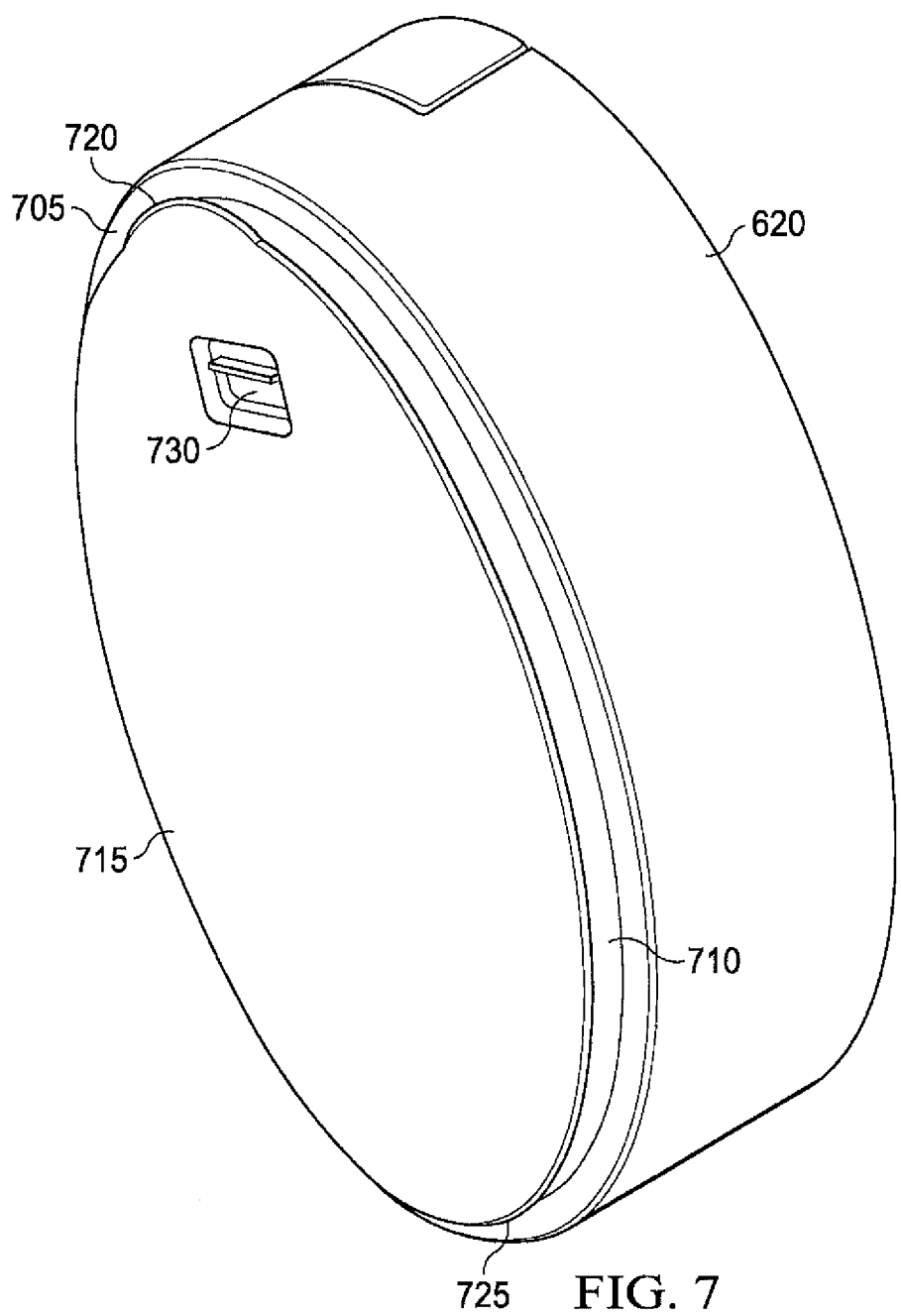
FIG. 7 illustrates a perspective view of a second end of the component module of FIG. 6.

FIG. 7 is a perspective view of a second end of the component module 600 illustrated in FIG. 6. This perspective view illustrates a configuration that is substantially similar to the configuration of the control unit 300 described above with reference to FIGS. 3-5, so that additional component modules may be connected in a chain or series as needed to expand the functionality of a reduced pressure treatment system. In particular, the component module 600 includes the outer surface 620 having a shoulder 705, an extension 710 fixed to the shoulder, and an end surface 715. The extension 710 further includes a first ridge 720 and a second ridge 725, which is generally located opposite the first ridge 720, and an aperture 730, through which a CAN port may be exposed to the exterior of the end surface 715.

Figure 8:
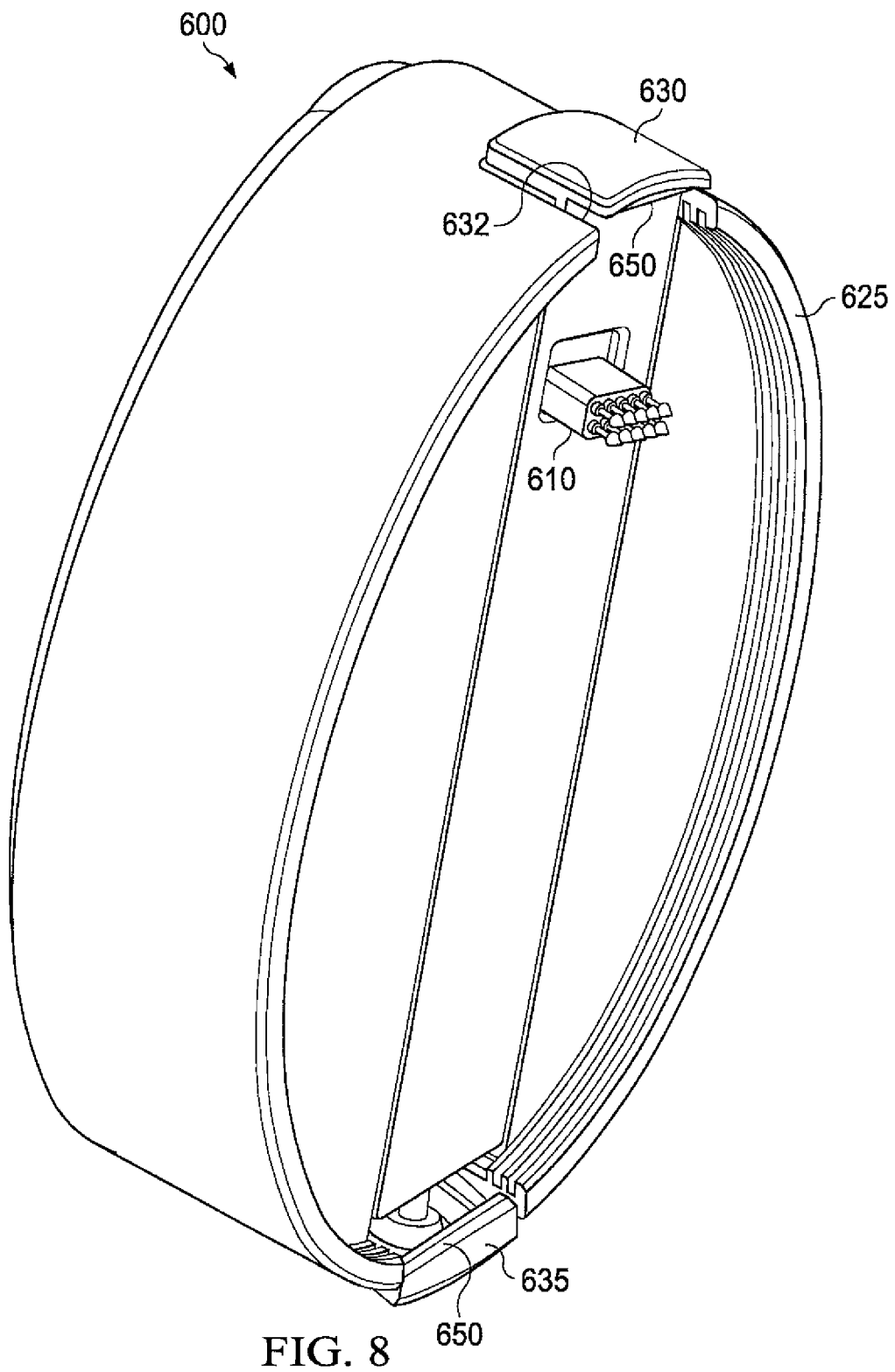
FIG. 8 illustrates a perspective view of the first end of the component module of FIG. 6 with extended latches.

Referring to FIG. 8 for illustration, the first latch 630 and the second latch 635 may be extended to mount the component module 600 to a control unit or another component module. In alternate embodiments, the first latch 630, the second latch 635, or both may be rotated about a pin so that only the fastener bar of the latch is extended. Extending the mounting assembly 625 allows the fastener bars 650 to be placed over the ridges on another component module or control unit, and then collapsed onto the extension to secure the component module 600.

Figure 9:
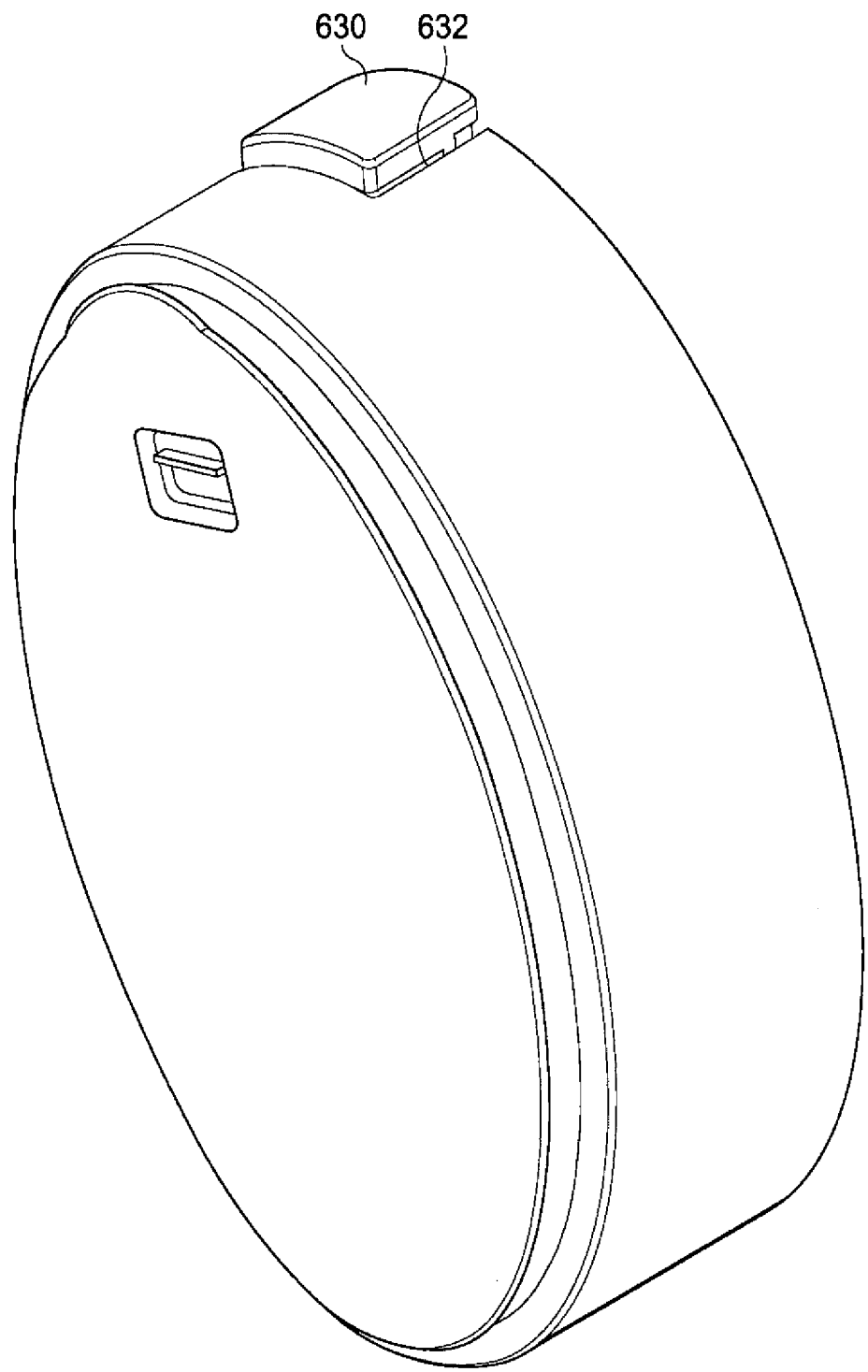
FIG. 9 illustrates a perspective view of the second end of the component module of FIG. 6 with extended latches.

FIG. 9 illustrates the second end of the component module 600 shown in FIG. 7, with the first latch 630 extended.

Figure 10:
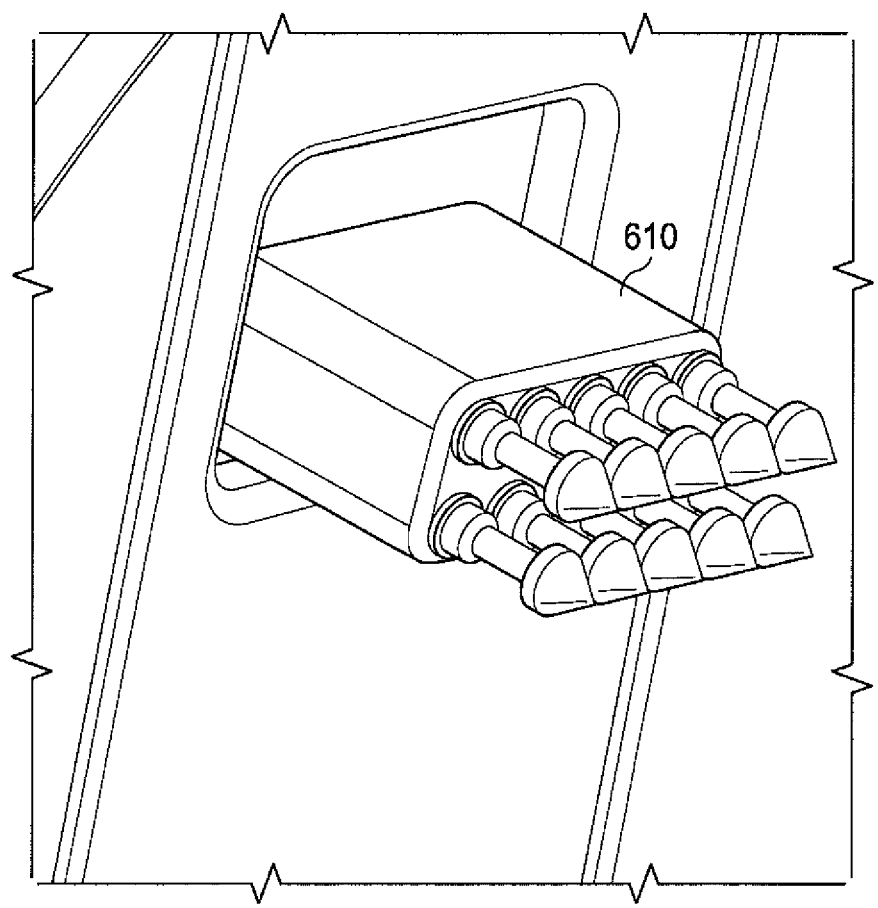
FIG. 10 illustrates an enlarged perspective view of a communication plug of the component module of FIG. 6.

FIG. 10 is an enlarged perspective view of an embodiment of a CAN plug 610. In this embodiment, the CAN plug 610 consists of a plurality of pin connectors that align with corresponding plate connectors in a CAN port. Each pin connector may be wired as desired to a control system within a component module.

It should be apparent from the foregoing that an invention having significant advantages has been provided. While the invention is shown in only a few of its forms, it is not so limited and is susceptible to various changes and modifications without departing from the spirit thereof.

We claim:

1. A method for treating a tissue site, the method comprising:
    coupling a first mounting region of a first component module to a complimentary mounting region of a control unit, the control unit having a control system configured to communicate with the first component module, and the first component module having a second mounting region adapted to be coupled with a second component module; and
    controlling the first component module with the control system of the control unit to treat the tissue site.

2. The method of claim 1, wherein the first mounting region further comprises a rim and a recessed end surface, and the method further comprises engaging the rim and the recessed end surface with the complimentary mounting region of the control unit.

3. The method of claim 2, wherein the first mounting region further comprises a mounting assembly having a latch, and the method further comprises engaging the mounting assembly and the latch with the complimentary mounting region of the control unit.

4. The method of claim 2, wherein the complimentary mounting region of the control unit further comprises a shoulder and an extension surface, the method further comprising engaging the shoulder and the extension surface with the first mounting region of the component module.

5. The method of claim 2, wherein:
    the first mounting region further comprises a rim, a recessed end surface, and a latch;
    the complimentary mounting region of the control unit further comprises a shoulder and an extension surface; and the method further comprises:
    receiving the extension surface with the recessed end surface; and
    fastening the latch to the extension surface to secure the component module to the control unit.

6. The method of claim 5, wherein the extension surface includes a ridge and the latch includes a fastener bar, the method further comprises securing the component module to the control unit by overlapping the ridge with the fastener bar.

7. The method of claim 2, wherein the method further comprises communicating between the first component module and the control system using a controller area network protocol.

8. The method of claim 2, wherein the control system further comprises a treatment controller and a communication controller.

9. A method for treating a tissue site of a patient, the method comprising:
    coupling a reduced pressure source to a control unit having a control system configured to control the reduced pressure source;
    providing a plurality of component modules to augment treatment, each of the plurality of component modules configured to communicate with the control system of the control unit;
    coupling a first component module to the control unit; and
    coupling a second component module to the first component module.

10. The method of claim 9, further comprising communicating between the plurality of component modules and the control system using a controller area network protocol.

11. The method of claim 9, wherein at least one of the component modules is a wound camera and the method further comprises imaging the tissue site.

12. The method of claim 9, wherein at least one of the component modules is a cyclic skin stretcher and the method further comprises cyclically stretching the tissue site.

13. The method of claim 9, wherein at least one of the component modules is a capacitive volume and wound contour mapping module and the method further comprises mapping contours of the tissue site.

14. The method of claim 9, wherein at least one of the component modules is a wound bed pH monitor and the method further comprises monitoring the pH of the tissue site.

15. The method of claim 9, wherein at least one of the component modules is a wound climate control module and the method further comprises controlling the climate of the tissue site.

16. The method of claim 9, wherein at least one of the component modules is a wound moisture and temperature monitor and the method further comprises monitoring moisture and temperature of the tissue site.

17. The method of claim 9, wherein at least one of the component modules is an electrical stimulation module and the method further comprises electrically stimulating the tissue site.

18. The method of claim 9, wherein at least one of the component modules is an ultraviolet therapy module and the method further comprises treating the tissue site with ultraviolet therapy.

19. The method of claim 9, wherein at least one of the component modules is a wound healing marker measurement module and the method further comprises measuring wound healing markers of the tissue site.

20. The method of claim 9, wherein the control system further comprises a treatment controller and a communication controller.

21. A system for treating a tissue site, the system comprising:
    a dressing configured to be positioned adjacent to a tissue site;
    a reduced pressure source configured to be fluidly connected to the dressing and having a control unit; and
    a treatment component module having a control system with a communication controller configured to communicate with the control unit.

22. The system of claim 21, wherein the communication controller is a controller area network controller.

23. The system of claim 21, wherein the treatment component module comprises:
   a housing having a rim, a recessed end surface, and an extension;
   a mounting assembly fixed to the recessed end surface, the mounting assembly comprising a fastener bar that is substantially flush with the rim when a first latch and a second latch are not extended;
   a first aperture through the mounting assembly and recessed end surface; and
   a second aperture through the extension.

24. The system of claim 23, wherein the extension comprises a first ridge and a second ridge opposite the first ridge.

25. The system of claim 23, wherein the second latch is configured to pivot about an axis to extend the fastener bar.

26. The system of claim 21, further comprising:
   a control system having a treatment controller and a communication controller;
   a communication port coupled to the communication controller;
   a reduced pressure source coupled to the treatment controller;
   a manifold unit in fluid communication with the reduced pressure source;
   a removable component module coupled to the control system through the communication port;
   a first housing that encloses the control system, the first housing comprising a shoulder and an extension surface;
   a second housing that encloses the component module, the second housing comprising a rim and a recessed end surface;
   a mounting assembly having a latch;
   a first aperture through the mounting assembly and the recessed end surface; and
   a second aperture through which the communication port is exposed to the extension surface, the second aperture aligned with the first aperture;
   wherein the recessed end surface receives the extension surface and the latch fastens to the extension surface to secure the second housing to the first housing.

27. The system of claim 26, wherein the extension surface comprises a ridge and the latch fastens to the ridge to secure the second housing to the first housing.

28. The system of claim 26, wherein the extension surface comprises a ridge and the latch comprises a fastener bar that overlaps the ridge to secure the second housing to the first housing.

29. The system of claim 26, wherein the extension surface comprises a first ridge and a second ridge, and the mounting assembly comprises a first fastener bar and a second fastener bar that overlap the first ridge and the second ridge to secure the second housing to the first housing.

30. The system of claim 26, wherein the first housing and second housing are substantially elliptic cylinders.

31. A control unit for a tissue treatment system, the control unit comprising:
   a housing;
   a communication controller disposed in the housing;
   an extension coupled to the housing and having an end surface, the extension configured to engage a component module; and
   a communication controller port coupled to the communication controller and exposed through an aperture in the end surface.

32. The control unit of claim 31, further comprising:
   a first ridge located on the end surface; and
   a second ridge located on the end surface opposite the first ridge.

33. The control unit of claim 32, wherein the first ridge and the second ridge are configured to engage a fastener bar of the component module.

34. The control unit of claim 31, wherein the component module is configured to communicate with the communication controller through the communication controller port.

35. The control unit of claim 31, wherein the component module comprises:
   a module housing having a rim, a recessed end surface, and an extension;
   a mounting assembly fixed to the recessed end surface, the mounting assembly comprising:
      a first latch, and
      a second latch, wherein the first latch and the second latch each comprise a fastener bar that is substantially flush with the rim when the first latch and the second latch are not extended; and
   a control system contained within the module housing, the control system having a module communication controller configured to communicate with the communication controller of the control unit.

36. The control unit of claim 35, wherein the communication controller and the module communication controller are controller area network controllers.

37. The control unit of claim 35, wherein the second latch pivots about an axis to extend the fastener bar.

38. A component module for treating a tissue site, the component module comprising:
   a housing having a rim, a recessed end surface, and an extension;
   a mounting assembly fixed to the recessed end surface, the mounting assembly comprising an extendable first latch and an extendable second latch;
   a first aperture through the mounting assembly and the recessed end surface;
   a second aperture through the extension;
   a control system contained within the housing, the control system having a communication controller;
   a communication plug coupled to the communication controller and protruding through the first aperture; and
   a communication port coupled to the communication controller and exposed to the second aperture.

39. The module according to claim 38, wherein the communication controller is a controller area network controller.

40. The module according to claim 38, wherein the extension comprises a first ridge and a second ridge opposite the first ridge.

41. The module according to claim 38, wherein the second latch pivots about an axis to extend a fastener bar.

* * * * *